United States Patent
Lee

(10) Patent No.: US 10,857,217 B2
(45) Date of Patent: *Dec. 8, 2020

(54) ANTIGEN FUSED WITH PORCINE FC FRAGMENT AND VACCINE COMPOSITION COMPRISING THE SAME

(71) Applicant: BIOAPPLICATIONS INC., Pohang-si (KR)

(72) Inventor: Yongjik Lee, Pohang-si (KR)

(73) Assignee: BIOAPPLICATIONS INC., Pohang-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/374,127

(22) Filed: Apr. 3, 2019

(65) Prior Publication Data

US 2020/0085926 A1    Mar. 19, 2020

Related U.S. Application Data

(63) Continuation of application No. PCT/KR2018/015399, filed on Dec. 6, 2018.

(30) Foreign Application Priority Data

Sep. 19, 2018 (KR) ........................ 10-2018-0112443

(51) Int. Cl.
| | |
|---|---|
| *A61K 39/00* | (2006.01) |
| *A61K 39/12* | (2006.01) |
| *A61K 39/29* | (2006.01) |
| *A61K 47/68* | (2017.01) |
| *C07K 14/705* | (2006.01) |
| *C07K 14/005* | (2006.01) |

(52) U.S. Cl.
CPC .......... *A61K 39/0005* (2013.01); *A61K 39/12* (2013.01); *A61K 39/29* (2013.01); *A61K 47/68* (2017.08); *C07K 14/005* (2013.01); *C07K 14/705* (2013.01); *A61K 2039/6056* (2013.01); *C07K 2319/30* (2013.01); *C12N 2750/10022* (2013.01); *C12N 2750/10034* (2013.01); *C12N 2770/24222* (2013.01); *C12N 2770/24234* (2013.01)

(58) Field of Classification Search
None
See application file for complete search history.

(56) References Cited

U.S. PATENT DOCUMENTS

2018/0305710 A1* 10/2018 An ........................ A61K 39/145
2020/0087351 A1*  3/2020 Lee ...................... C07K 14/705

FOREIGN PATENT DOCUMENTS

CN         106519041 A  *  3/2017  ............. C12N 15/85
WO    WO-2017195919 A1 * 11/2017  ........... A61K 39/145

OTHER PUBLICATIONS

Invitrogen (pcDNA™ 3.1(+), pcDNA™ 3.1(−), User Manual, Version K, Nov. 10, 2010) (Year: 2010).*

* cited by examiner

*Primary Examiner* — Peter J Reddig
(74) *Attorney, Agent, or Firm* — Vorys, Sater, Seymour & Pease LLP; Mih Suhn Koh

(57) ABSTRACT

Provided is an antigen fused with a porcine Fc fragment, a vaccine composition having a self-adjuvanting effect by binding an Fc fragment to various antigens, and a method of producing the antigen.

11 Claims, 10 Drawing Sheets

Specification includes a Sequence Listing.

FIG. 2

| p35S | M17 | BiP | VP1 | pFc | HDEL | NOS |

FIG. 4

ANTIGEN FUSED WITH PORCINE FC FRAGMENT AND VACCINE COMPOSITION COMPRISING THE SAME

CROSS-REFERENCE TO RELATED APPLICATION

This application is a Continuation of PCT/KR2018/015399, filed Dec. 6, 2018, which claims the benefit of priority from Korean Patent Application No. 10-2018-0112443, filed Sep. 19, 2018, the contents of each of which are incorporated herein by reference in its entirety.

SEQUENCE LISTING

The Sequence Listing submitted in text format (.txt) filed on Aug. 29, 2019, named "SequenceListing.txt", created on Aug. 29, 2019 (23.3 KB), is incorporated herein by reference.

TECHNICAL FIELD

The present invention relates to an antigen fused with a porcine Fc fragment, a vaccine composition including the antigen, and the like.

BACKGROUND ART

Vaccines for the prevention of infectious diseases induce specific and effective immune responses against pathogens, and the need for vaccines continues to increase to prevent various infectious diseases. Recently, various types of vaccines such as a killed vaccine, attenuated live vaccine, autogenous vaccine, and the like have been developed. In this regard, vaccines produced from live bacteria or attenuated bacteria are very effective in terms of prevention, but safety problems have often been reported due to problems such as risk of regression, self-replication, and the like, and vaccines using dead bacteria contain toxic materials such as lipopolysaccharides (LPSs), or have a risk that living bacteria may be present. Therefore, the possibility of DNA vaccines, which have been developed to address these limitations, to function mutagenically or oncogenically by insertion onto the genome of a host has also been raised. Therefore, the development of subunit vaccines using purified antigens has recently been actively performed. Such subunit vaccines are more stable than other vaccines due to the use of purified antigens, but have poor immunogenicity, thus requiring potent adjuvants to enhance immunogenicity. The use of adjuvants can significantly reduce the amount of antigen used, and thus it may not only play a decisive role in rapid production of vaccines under circumstances such as the spread of epidemics but may also reduce the number of additional vaccinations, and the like, resulting in significantly reduced costs and inconvenience. However, very few adjuvants have been approved for use in vaccines. The first adjuvant "alum" was approved in 1932 for use in human vaccines, and has been most widely used to date. Since then, MF59, AS03, and the like have been developed and licensed, but there are still very few adjuvants licensed for use in vaccines (Korean Patent Registration No. 10-0517114).

Therefore, the development of adjuvants that not only significantly increase the immunogenicity of vaccines, but also are stable is expected to play a very important role in the development of the vaccine field.

DISCLOSURE

Technical Problem

The present invention has been made to address the above-described problems, and it is an object of the present invention is to provide an antigen fused with a porcine Fc fragment, a vaccine composition including the antigen, and a method of preparing the antigen.

However, technical problems to be solved by the present invention are not limited to the above-described technical problems, and other unmentioned technical problems will become apparent from the following description to those of ordinary skill in the art.

Technical Solution

The present invention provides a vaccine composition including, as an active ingredient, an antigen fused with a porcine Fc fragment represented by SEQ ID NO: 4.

The present invention also provides a method of preventing or treating an infectious disease, which includes administering, to an individual, a composition including an antigen fused with a porcine Fc fragment represented by SEQ ID NO: 4, as an active ingredient.

The present invention also provides a use of a composition including, as an active ingredient, an antigen fused with a porcine Fc fragment represented by SEQ ID NO: 4 for preventing or treating an infectious disease.

In one embodiment of the present invention, the antigen may have a self-adjuvanting effect and increased solubility by fusion with an Fc fragment. The fusion may be a form in which an antigen is linked to the N-terminus and/or the C-terminus of an Fc fragment via a peptide bond, but it is not particularly limited as long as it is a form in which an Fc fragment and an antigen are bound.

The present invention also provides an expression vector of a recombinant antigen having a self-adjuvanting effect, the expression vector including a polynucleotide encoding a porcine Fc fragment represented by SEQ ID NO: 4 and a polynucleotide encoding an antigen.

In one embodiment of the present invention, in the expression vector, a promoter gene, the polynucleotide encoding an Fc fragment, and the polynucleotide encoding an antigen; or a promoter gene, the polynucleotide encoding an antigen, and the polynucleotide encoding an Fc fragment may be sequentially linked in this order.

In another embodiment of the present invention, a promoter is a 35S promoter derived from cauliflower mosaic virus, a 19S RNA promoter derived from cauliflower mosaic virus, an actin protein promoter of a plant, an ubiquitin protein promoter, a cytomegalovirus (CMV) promoter, a simian virus 40 (SV40) promoter, a respiratory syncytial virus (RSV) promoter, an elongation factor-1 alpha (EF-1α) promoter, a pEMU promoter, an MAS promoter, a histone promoter, or a Clp promoter, but the present invention is not limited thereto.

In another embodiment of the present invention, an antigen protein may be an antigen, an antibody, an antibody fragment, a structural protein, a regulatory protein, a transcription factor, a toxin protein, a hormone, a hormone analogue, a cytokine, an enzyme, an enzyme fragment, an enzyme inhibitor, a transport protein, a receptor, a fragment of a receptor, a bio-defense inducer, a storage protein, a movement protein, an exploitive protein, or a reporter protein, but is not particularly limited as long as it is capable of inducing an immune response by acting as an antigen in vivo.

In another embodiment of the present invention, the expression vector may further include a polynucleotide encoding a chaperone binding protein (BiP), a gene encoding a His-Asp-Glu-Leu (HDEL) (SEQ ID NO: 20) peptide, a 5' untranslated region (UTR) site gene of M17, or the like.

In another embodiment of the present invention, the expression vector increases an expression amount of a target antigen to which an Fc fragment is fused and increases the solubility of the target antigen.

The present invention also provides a transgenic organism transformed with the expression vector.

In one embodiment of the present invention, the transgenic organism may be a microorganism such as *Escherichia coli, Bacillus, Salmonella*, yeast, or the like, insect cells, animal cells including human cells, an animal such as a mouse, a rat, a dog, a monkey, a pig, a horse, a cow, or the like, *Agrobacterium tumefaciens*, a plant, or the like, and examples of the plant include food crops including rice, wheat, barley, corn, beans, potatoes, red beans, oats, and sorghum; vegetable crops including *Arabidopsis thaliana*, Chinese cabbage, white radish, peppers, strawberries, tomatoes, water melons, cucumbers, cabbage, oriental melons, pumpkins, spring onions, onions, and carrots; special purpose crops including *ginseng*, tobacco, cotton, sesame, sugarcane, sugar beets, *perilla*, peanuts, and rape; fruit crops including apple trees, pear trees, jujube trees, peaches, grapes, tangerines, persimmons, plums, apricots, and bananas; and flowers including roses, carnations, chrysanthemums, lilies, and tulips, but it is not particularly limited as it is a living body capable of being transformed with the expression vector of the present invention.

In addition, the present invention also provides a method of producing a recombinant antigen, which includes: (a) culturing the transgenic organism; and (b) isolating and purifying an antigen fused with an Fc fragment from the transgenic organism or a culture broth. The transgenic organism may be preferably a cell itself or a cell-containing culture, and the culture broth may be preferably a culture broth obtained by culturing cells and removing the cells, but the present invention is not limited thereto, and any culture broth including the recombinant antigen of the present invention may be used.

Advantageous Effects

An antigen fused with a porcine Fc fragment according to the present invention has a self-adjuvanting effect, and thus the immunogenicity of an antigen itself can be increased without using an additional adjuvant, and the solubility and stability of an antigen can be increased, thus facilitating the separation and storage of an antigen. In addition, in an expression vector according to the present invention, the productivity of a target antigen can be increased by fusing pFc with various antigens, and thus it is anticipated that the expression vector enables high-efficiency production of vaccines.

DESCRIPTION OF DRAWINGS

FIG. 2 is a view illustrating arrangement of genes for expressing a pFc-fused VP1 recombinant protein according to an embodiment of the present invention.

FIG. 4 illustrates western blotting results of confirming the stability of a pFc-fused VP1 recombinant protein according to an embodiment of the present invention.

BEST MODE

Figure 1:
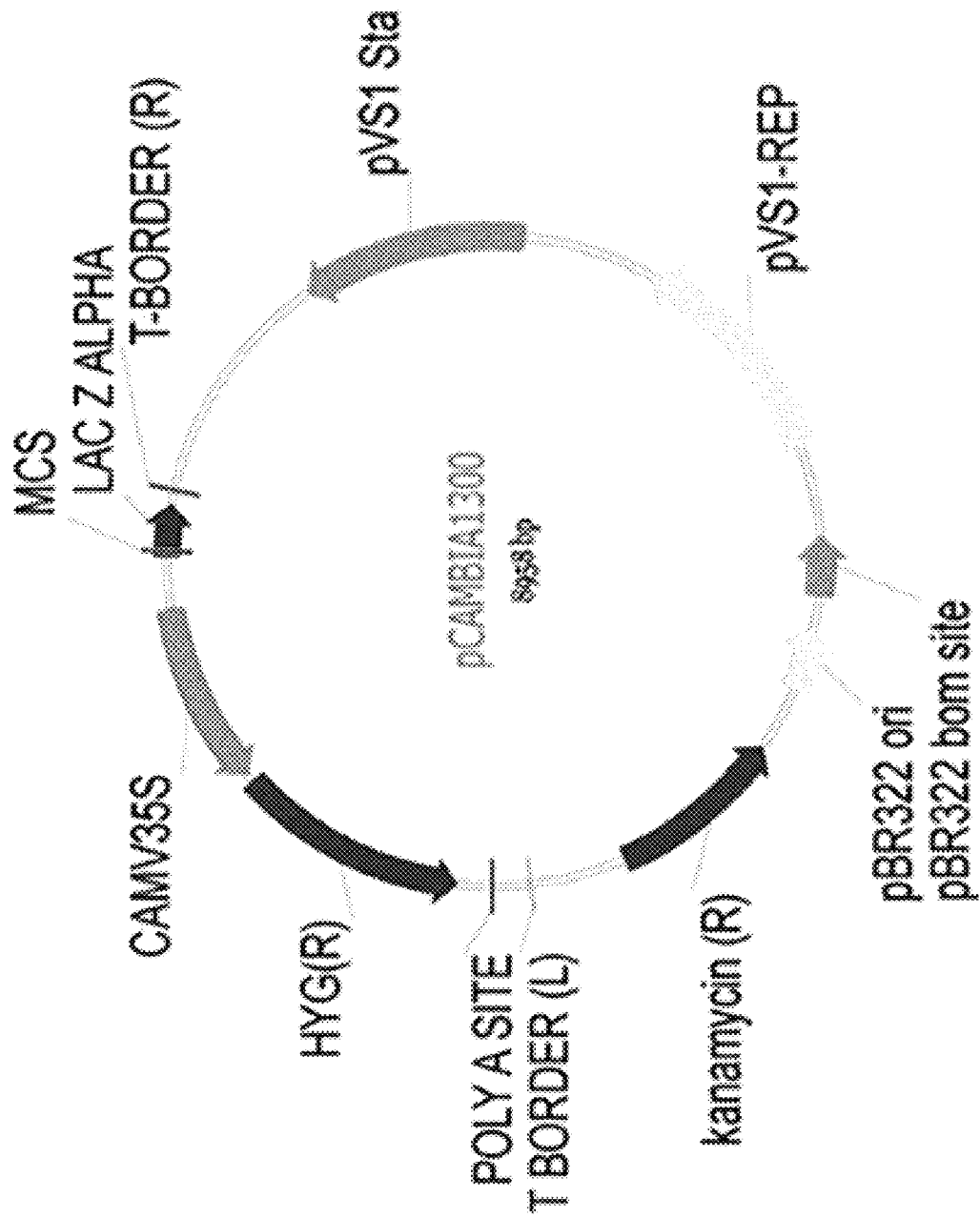
FIG. 1 is a view illustrating a pCAMBIA1300 vector map according to an embodiment of the present invention.

In the present invention, it has been confirmed that, when various antigens are bound to a porcine Fc fragment, not only an expression amount and productivity but also solubility and stability of an antigen are increased by the fragment, and it is an object of the present invention is to provide an antigen fused with the porcine Fc fragment, an expression vector including a polynucleotide encoding the porcine Fc fragment and a polynucleotide encoding an antigen, and a method of producing a recombinant antigen using the expression vector.

As used herein, the term "Fc fragment" refers to an Fc fragment not having an antigen binding site, in which only a heavy chain (H chain) portion is linked by an S—S bond, when an immunoglobulin is digested with papain, and the Fc fragment of the present invention is preferably a porcine Fc fragment, more preferably a porcine Fc fragment represented by SEQ ID NO: 4, but the present invention is not limited thereto, and any Fc fragment that increases the expression amount and solubility of a target antigen when fused with the target antigen may be used. In addition, a variant of the Fc fragment of SEQ ID NO: 4 of the present invention is within the scope of the present invention. Specifically, the gene may include a base sequence having 90% or more, preferably 95% or more, and more preferably 98% or more sequence homology to the base sequence of SEQ ID NO: 3. The "% sequence homology" with respect to a polynucleotide is determined by comparing optimally-arranged sequences with a comparative region, and a part of the polynucleotide sequence in the comparative region may include an addition or deletion (i.e., a gap) compared to a reference sequence (without an addition or deletion) with respect to the optimal arrangement of the sequences.

As used herein, the term "antigen" collectively refers to any substance inducing immune responses in vivo, and the antigen is preferably a virus, a compound, a bacterium, pollen, a cancer cell, a shrimp, or a peptide or protein of a part thereof, but is not particularly limited as long as it is a substance capable of inducing an immune response in vivo.

As used herein, the term "vaccine" refers to a biological agent including an antigen that causes an immune response in vivo and an immunogen that causes the living body to have immunity via injection or oral administration thereof to a human or an animal to prevent infectious diseases. The animal refers to humans or non-human animals, and the non-human animals refer to pigs, cows, horses, dogs, goat, and sheep, but the present invention is not limited thereto.

As used herein, the term "target protein" refers to a protein to be produced using a genetic engineering method, and the target protein may be preferably commercially available antigens in need of mass production and more preferably, an antigen, an antibody, an antibody fragment, a structural protein, a regulatory protein, a transcription factor, a toxin protein, a hormone, a hormone analogue, a cytokine, an enzyme, an enzyme fragment, an enzyme inhibitor, a transport protein, a receptor, a receptor fragment, a biodefense inducer, a storage protein, a movement protein, an exploitive protein, or a reporter protein, but the present invention is limited thereto, and any protein capable of being produced with the expression vector of the present invention may be used.

As used herein, the term "expression vector" refers to a vector capable of expressing a peptide or protein encoded by a heterologous nucleic acid inserted into the vector, and preferably means a vector constructed so as to express a porcine Fc fragment-fused target antigen. The term "vector" as used herein refers to any vehicle for the introduction and/or transfer of a base into a host cell in vitro, ex vivo, or in vivo, and may mean a replicon to which another DNA fragment may be attached so as to bring about the replication of the attached fragment. The term "replicon" refers to any genetic unit (e.g., a plasmid, a phage, a cosmid, a chromosome, a virus, and the like) that functions as an autonomous unit of DNA replication in vivo, i.e., is capable of replicating by self-regulation. The expression vector of the present invention may preferably include a promoter which is a transcription initiation factor to which an RNA polymerase binds, an arbitrary operator sequence for regulating transcription, a sequence encoding a suitable mRNA ribosome binding site, a sequence regulating the termination of transcription and translation, a terminator, or the like. More preferably, the expression vector may further include a 5' UTR site gene of M17, a BiP gene for transporting a target protein to a vesicle, an HDEL (SEQ ID NO: 20) gene for minimizing the degradation of a protein so that the protein can be stably maintained in a vesicle, or the like. More preferably, the expression vector may further include a gene for a tag for easily isolating a recombinant protein, a marker gene for selecting an antibiotic-resistant gene or the like to select a transgenic organism, or the like.

The gene for a tag may be additionally included for easy separation, other than the Fc fragment of the present invention, which is a tag protein, and examples thereof may include an Avi tag, a Calmodulin tag, a polyglutamate tag, an E tag, a FLAG tag, a HA tag, a His tag, a Myc tag, an S tag, an SBP tag, an IgG-Fc tag, a CTB tag, a Softag 1 tag, a Softag 3 tag, a Strep tag, a TC tag, a V5 tag, a VSV tag, an Xpress tag, and the like. Examples of the marker gene for selection may include genes resistant to herbicide such as glyphosate and phosphinothricin, genes resistant to antibiotics such as kanamycin, G418, bleomycin, hygromycin, and chloramphenicol, the aadA gene, and the like, examples of the promoter may include a pEMU promoter, an MAS promoter, a histone promoter, a Clp promoter, a 35S promoter derived from cauliflower mosaic virus, a 19S RNA promoter derived from cauliflower mosaic virus, an actin protein promoter of a plant, an ubiquitin protein promoter, a cytomegalovirus (CMV) promoter, a simian virus 40 (SV40) promoter, a respiratory syncytial virus (RSV) promoter, an elongation factor-1 alpha (EF-1α) promoter, and the like, and examples of the terminator may include nopaline synthase (NOS), a rice amylase RAmyl A terminator, a phaseolin terminator, an Octopine gene terminator of *Agrobacterium tumefaciens*, and an *E. coli* rrnB1/B2 terminator, but these are merely examples and the present invention is not limited thereto.

As used herein, the term "fusion antigen" refers to a recombinant protein produced by fusion of a porcine Fc fragment and a target antigen, and preferably means a recombinant antigen with enhanced solubility through fusion with the Fc fragment, but the present invention is not limited thereto, and any recombinant antigen produced through binding with a porcine Fc fragment may be used.

As used herein, the term "transformation" collectively refers to changes in the genetic properties of an organism by injected DNA, and the term "transgenic organism" refers to a living organism produced by injecting an external gene using a molecular genetic method, and preferably means a living organism transformed by the expression vector of the present invention. The living organism is not particularly limited as long as it is a living organism such as microorganisms, eukaryotic cells, insects, animals, plants, and the like, and examples thereof include, but are not limited to, *E. coli, Salmonella, Bacillus*, yeast, animal cells, mice, rats, dogs, monkeys, pigs, horses, cows, *Agrobacterium tumefaciens*, and plants. The transgenic organism may be produced using a method such as transformation, transfection, an *Agrobacterium*-mediated transformation method, particle gun bombardment, sonication, electroporation, and a polyethylene glycol (PEG)-mediated transformation method, but the present invention is not limited thereto, and any method capable of injecting the vector of the present invention may be used.

As used herein, the term "solubility" refers to a degree to which a target protein or a peptide can be dissolved in a solvent suitable for administration to the human body. Specifically, the solubility may indicate a degree to which a solute is saturated with respect to a given solvent at a particular temperature. The solubility may be measured by determining the saturation concentration of a solute, for example, by adding an excess amount of a solute to a solvent and stirring and filtering the solution, and then measuring the concentration thereof using a UV spectrometer, HPLC, or the like, but the present invention is not limited thereto. High solubility is more suitable for the isolation and purification of recombinant proteins, and inhibits the agglomeration of recombinant proteins, and thus it is effective in maintaining the physiological activity or pharmacological activity of recombinant proteins.

As used herein, the term "prevention" means all actions that inhibit or delay the onset of a disease such as an infectious disease, cancer, or the like via administration of the vaccine composition according to the present invention.

As used herein, the term "treatment" means all actions that improve or beneficially change symptoms of an infectious disease, cancer, or the like via administration of the vaccine composition according to the present invention.

As used herein, the term "individual" refers to a subject to which the vaccine composition of the present invention may be administered, and the subject is not particularly limited.

The vaccine composition of the present invention may be formulated into oral preparations such as powder, granules, tablets, capsules, suspensions, emulsions, syrups, aerosols, and the like, and sterile injectable solutions. The formulation may be performed using commonly used diluents or excipients such as fillers, extenders, binders, wetting agents, disintegrating agents, surfactants, or the like. Solid preparations for oral administration include tablets, pills, powder, granules, capsules, and the like, and these solid preparations may be formulated by mixing a lecithin-like emulsifier with at least one excipient, for example, starch, calcium carbonate, sucrose, lactose, gelatin, or the like. In addition to simple excipients, lubricants such as magnesium stearate and talc may also be used. Liquid preparations for oral administration may include suspensions, liquids for internal use, emulsions, syrups, and the like, and these liquid preparations may include, in addition to simple commonly used diluents, such as water and liquid paraffin, various types of excipients, for example, a wetting agent, a sweetener, a flavoring agent, a preservative, and the like. Preparations for parenteral administration include an aqueous sterile solution, a non-aqueous solvent, a suspension, an emulsion, and a freeze-dried preparation. Non-limiting examples of the non-aqueous solvent and the suspension include propylene glycol, polyethylene glycol, vegetable oil such as olive oil, and an injectable ester such as ethyl oleate. In addition, the vaccine composition may further include a known adjuvant. Although any adjuvant known in the art may be used as the adjuvant without limitation, the vaccine composition may further include, for example, Freund' complete adjuvant or incomplete adjuvant to increase the immunogenicity thereof.

The vaccine composition of the present invention may be formulated in the form of oral preparations such as powder, granules, tablets, capsules, suspensions, emulsions, syrups, aerosols, and the like, preparations for external application, suppositories, and sterile injection solutions, according to general methods.

Administration routes of the vaccine composition according to the present disclosure include, but are not limited to, oral administration, intravenous administration, intramuscular administration, intra-arterial administration, intramedullary administration, intradural administration, intracardiac administration, transdermal administration, subcutaneous administration, intraperitoneal administration, intranasal administration, intestinal administration, topical administration, sublingual administration, and rectal administration. The vaccine composition may be administered orally or parenterally. The term "parenteral" as used herein is intended to include subcutaneous, intradermal, intravenous, intramuscular, intra-articular, intrabursal, intrasternal, intradural, intralesional, and intracranial injections or injection techniques. The vaccine composition of the present invention may also be administered in the form of a suppository for rectal administration.

A dose of the vaccine composition according to the present invention is selected in consideration of the age, body weight, gender, physical condition, and the like of an individual. An amount required to induce an immunoprotective response in an individual without any side effects may vary depending on the presence of recombinant proteins as immunogens and excipients. Generally, each dose includes the recombinant protein of the present invention in an amount of 0.1 μg to 1,000 μg, preferably 0.1 μg to 100 μg, with respect to 1 ml of a sterile solution thereof. If needed, arbitrarily repeated antigen stimulation may be performed after an initial dose of the vaccine composition.

As used herein, the term "adjuvant" generally refers to any substance that increases humoral and/or cellular immune responses against an antigen, and the term "self-adjuvanting response" means a response in which a recombinant antigen itself increases humoral and/or cellular immune responses against an antigen, as compared to existing antigens, and preferably means increasing immunogenicity of an antigen by binding the antigen to a porcine Fc fragment.

Hereinafter, exemplary embodiments will be described to aid in understanding the present invention. However, the following examples are provided only to facilitate the understanding of the present invention and are not intended to limit the scope of the present invention.

EXAMPLES

Example 1: Preparation of pFc-Fused VP1 Recombinant Protein Expression Vector

Figure 2:
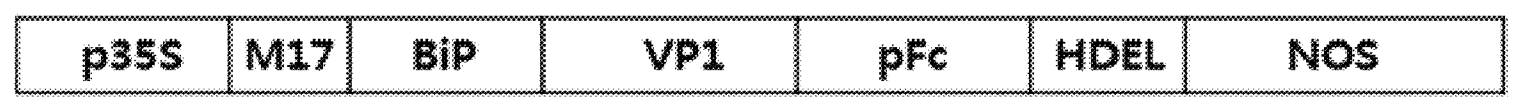

To prepare an expression vector for producing a recombinant protein with increased separation and purification efficiency through an increase in expression amount of a target protein and enhancement of the solubility thereof, pFc1 (SEQ ID NO: 1), pFc2 (SEQ ID NO: 3), or pFc3 (SEQ ID NO: 5) of a porcine Fc fragment (pFc) was used to construct an expression vector. More specifically, as illustrated in FIGS. 1 and 2, a 5' untranslated region (UTR) site gene (SEQ ID NO: 7) of M17, a polynucleotide (SEQ ID NO: 8) encoding a chaperone binding protein (BiP), a VP1 gene (SEQ ID NO: 9) of the foot-and-mouth disease virus (FMDV), a polynucleotide encoding a pFc, and a polynucleotide encoding a His-Asp-Glu-Leu (HDEL) (SEQ ID NO: 20) protein were sequentially cloned into between a CaMV 35S promoter gene and an NOS terminator of a pCAMBIA1300 vector, thereby completing the preparation of an expression vector. For the pFc fragment, different expression vectors were prepared by inserting pFc1, pFc2, or pFc3.

Example 2: Experiment for pFc-Fused VP1 Recombinant Protein Expression

2.1. Experiment for Confirming Expression Amount of pFc-Fused VP1 Recombinant Protein To identify protein expression amounts of a pFc-fused VP1 recombinant protein expression vector prepared in the same manner as in Example 1, the vector was introduced into a protoplast isolated from *Arabidopsis* leaves by PEG-mediated transformation to prepare a transgenic organism, and then the cultured protoplast was collected and lysed, and an expression pattern of BiP:FMDV-VP1:pFc, which is a recombinant protein expressed therefrom, was confirmed by western blotting using a pFc-recognizing anti-pig secondary antibody (1:5,000, Abcam). More specifically, 30 μL of a cell lysate was mixed with an SDS sample buffer and then heated. Then, proteins were separated on a 10% SDS-PAGE gel according to size by electrophoresis, the separated proteins were transferred to a PVDF membrane, followed by blocking using 5% skim milk, and then the proteins were subjected to binding to antibodies and treated with an ECL solution using a method provided by a manufacturer to identify pFc-fused recombinant proteins. The results thereof are illustrated in FIG. 3.

Figure 3:
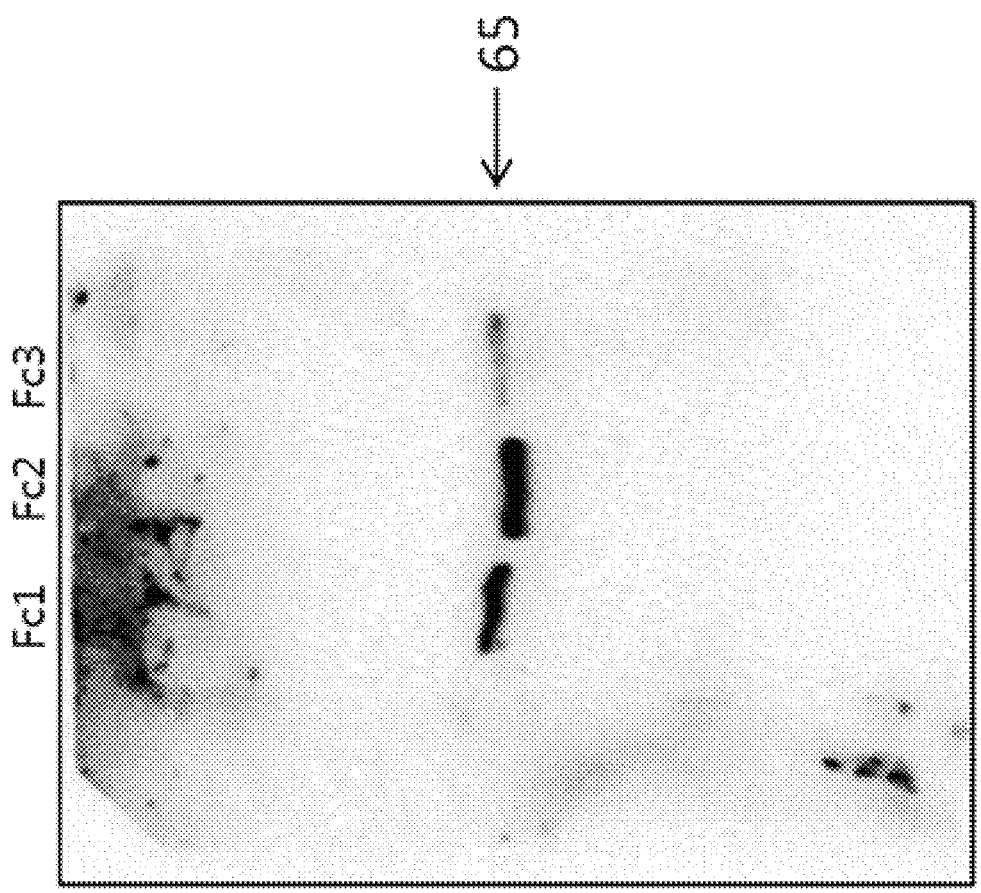
FIG. 3 illustrates western blotting results of confirming an expression amount of a pFc-fused VP1 recombinant protein according to an embodiment of the present invention.

As illustrated in FIG. 3, it was confirmed that the expression amount of the pFc2-fused recombinant protein was highest among the recombinant proteins fused with various pFc fragments. From the above results, it was confirmed that the same immunoglobulin fragments did not exhibit the same effect.

2.2. Stability Confirmation Experiment for pFc-Fused VP1 Recombinant Protein To confirm the stability of proteins of a pFc-fused recombinant protein expression vector prepared in the same manner as in Example 1, a sample (0) at the time of extracting the recombinant proteins and a sample (1) obtained after storage at 4° C. for 1 hour were examined by western blotting using the same method as that used in Example 2.1. The results thereof are illustrated in FIG. 4.

Figure 4:
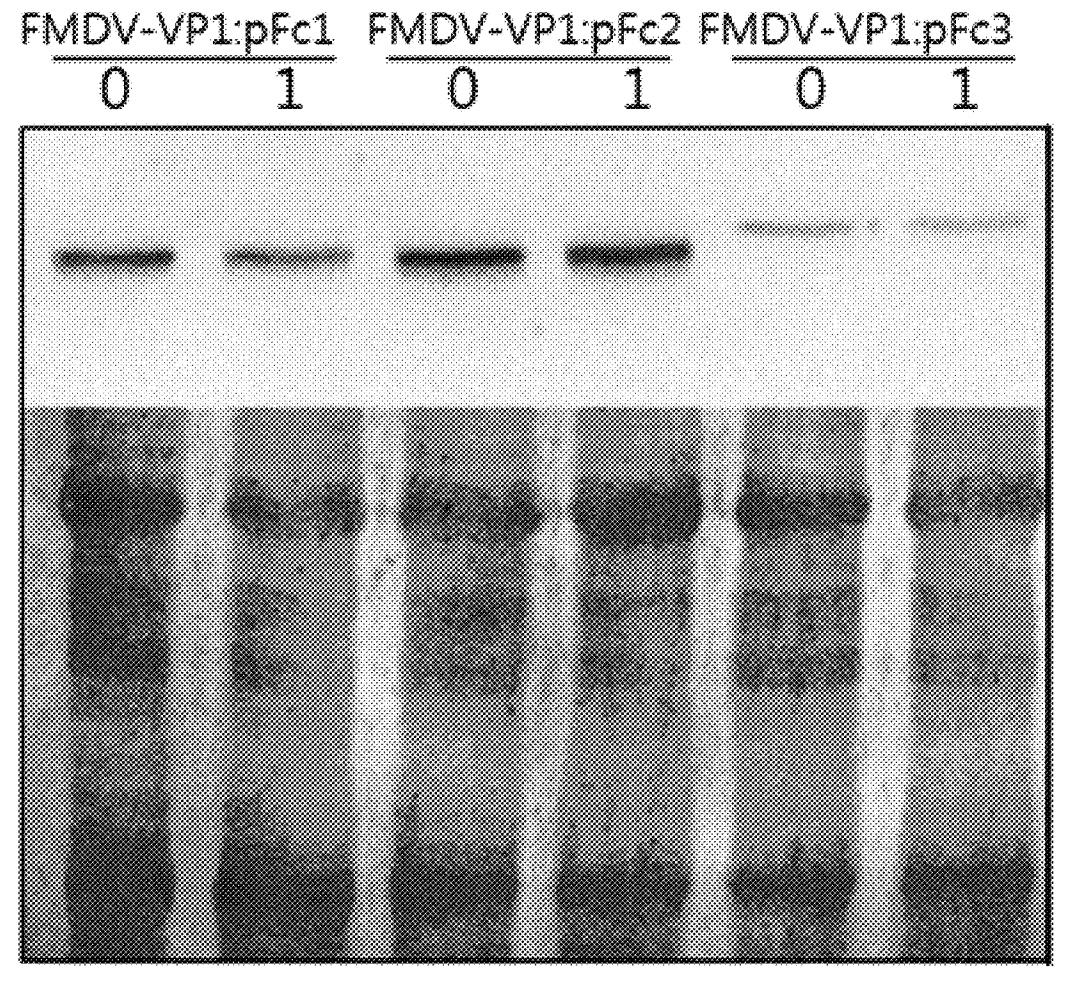

As illustrated in FIG. 4, it was confirmed that the pFc2-fused recombinant protein exhibited the greatest expression amount and high stability.

2.3. Solubility Confirmation Experiment for pFc2-Fused VP1 Recombinant Protein To confirm the solubility of proteins of a pFc2-fused recombinant protein expression vector prepared in the same manner as in Example 1, leaves of *Nicotiana benthamiana* were inoculated with *Agrobacterium tumefaciens* transformed with the vector to express the pFc2-fused recombinant protein (BiP:FMDV-VP1:pFc2) using a transient expression method, proteins were extracted from the plant leaves and centrifuged, and then proteins in a soluble form (S) included in a solution and proteins present in a pellet portion (P) were subjected to western blotting using the same method as that used in Example 2.1. As a control, recombinant proteins produced through fusion of a polynucleotide (SEQ ID NO: 13) encoding a known cellulose binding module (CBM3) instead of the pFc fragment was used. The results thereof are illustrated in FIG. 5.

Figure 5:
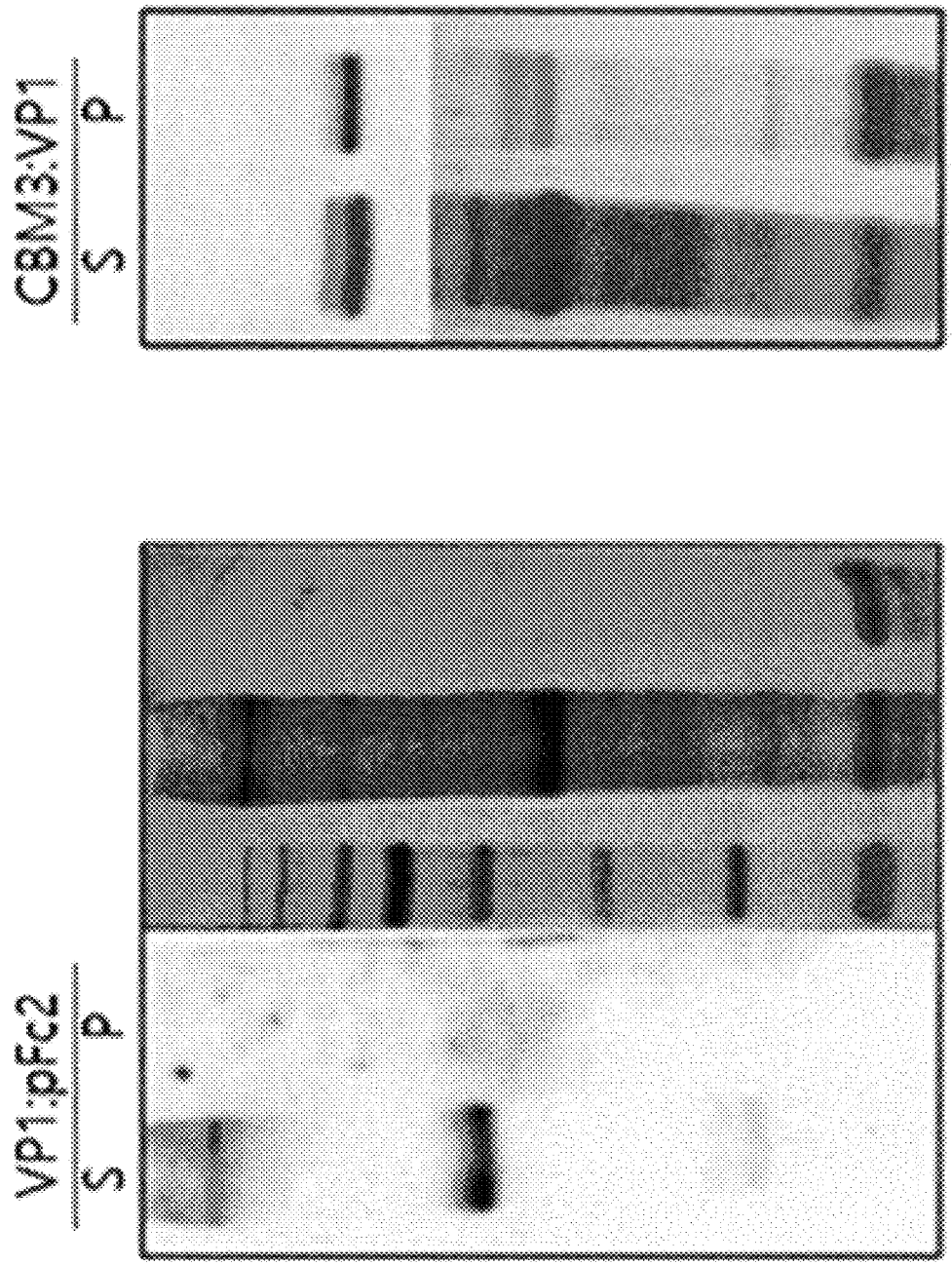
FIG. 5 illustrates western blotting results of confirming the solubility of a pFc-fused VP1 recombinant protein according to an embodiment of the present invention.

As illustrated in FIG. 5, it was confirmed that the pFc2-fused recombinant protein was not observed in the pellet portion, while being included in the solution. However, in the case of the CBM3-fused recombinant proteins, a considerable number of recombinant proteins were observed in the pellet portion. From the above results, it was confirmed that the pFc2-fused recombinant protein exhibited increased solubility through structural modification due to binding between a target protein and a pFc2 fragment, from which it was confirmed that the pFc2-fused recombinant protein was more effective in isolation and purification, and was effective in maintaining physiological activity or pharmacological activity due to inhibition of the agglomeration of the recombinant protein.

Example 3: Solubility Confirmation Experiment for pFc2-Fused GP5 Recombinant Antigen To fuse the pFc2 fragment with a GP5 antigen protein of porcine reproductive and respiratory syndrome (PRRS), a polynucleotide (SEQ ID NO: 11) encoding the porcine GP5 antigen protein was inserted instead of the VP1 gene of FMDV included in the expression vector of Example 1 to prepare an expression vector expressing a GP5:pFc2 recombinant antigen. Then, leaves of *Nicotiana benthamiana* were inoculated with *Agrobacterium tumefaciens* transformed with the vector to express the pFc2-fused GP5 recombinant antigen (GP5:pFc2) using a transient expression method, proteins were extracted from the plant leaves and centrifuged, and then proteins in a soluble form (S) included in a solution and proteins present in a pellet portion (P) were subjected to western blotting using the same method as that used in Example 2.1. As a control, a GP5 recombinant antigen fused with CBM3 (SEQ ID NO: 14) instead of the pFc fragment was used, and in the case of the CBM3-fused GP5 recombinant antigen, an experiment was carried out using an HA antibody for western blotting. The results thereof are illustrated in FIG. 6.

Figure 6:
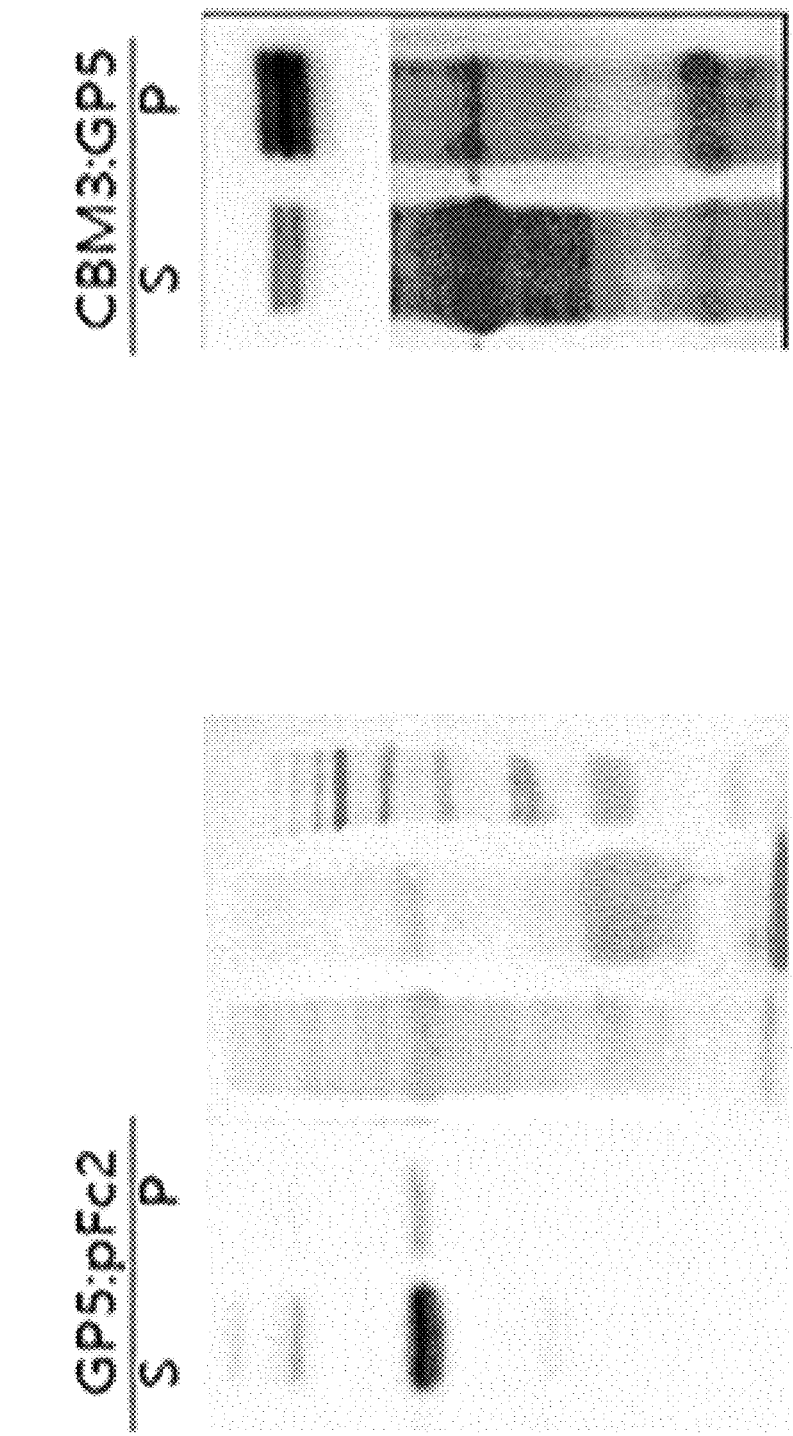
FIG. 6 illustrates western blotting results of confirming the solubility of pFc-fused GP5 recombinant antigen according to an embodiment of the present invention.

As illustrated in FIG. 6, it was confirmed that in the case of the pFc2-fused GP5 recombinant antigen, while some proteins were observed in the pellet portion, most proteins were included in the solution. In contrast, in the case of the CBM3-fused GP5 recombinant antigen, a considerable number of recombinant proteins were observed in the pellet portion. From the above results, it was confirmed that the pFc2-fused recombinant protein exhibited increased solubility regardless of the type of protein.

From these results, it was confirmed that by fusing a porcine Fc fragment, especially a pFc2 fragment including an amino acid sequence represented by SEQ ID NO: 4 with a target protein, the expression amount and solubility of the target protein were increased, and thus the target protein could be stably and easily separated and stored.

Example 4: Productivity and Solubility Confirmation Experiment for pFc2-Fused PCV2 Recombinant Protein To fuse the pFc2 fragment with a porcine circovirus type 2 (PCV2) protein, a polynucleotide (SEQ ID NO: 15) encoding the PCV2 protein was inserted instead of the VP1 gene of FMDV included in the expression vector of Example 1 to prepare an expression vector expressing a PCV2:pFc2 recombinant protein. Then, leaves of *Nicotiana benthami-* ana were inoculated with *Agrobacterium tumefaciens* transformed with the vector to express the pFc2-fused PCV2 recombinant protein using a transient expression method, proteins were extracted from the plant leaves and centrifuged, and then proteins in a soluble form (S) included in a solution and proteins present in a pellet portion (P) were subjected to western blotting using the same method as that used in Example 2.1. As a control, a PCV2 recombinant protein fused with His-tag instead of the pFc fragment was used, and in the case of the His-tag-fused PCV2 recombinant protein, an experiment was carried out using an anti-His antibody for western blotting. The results thereof are illustrated in FIG. 7.

Figure 7:
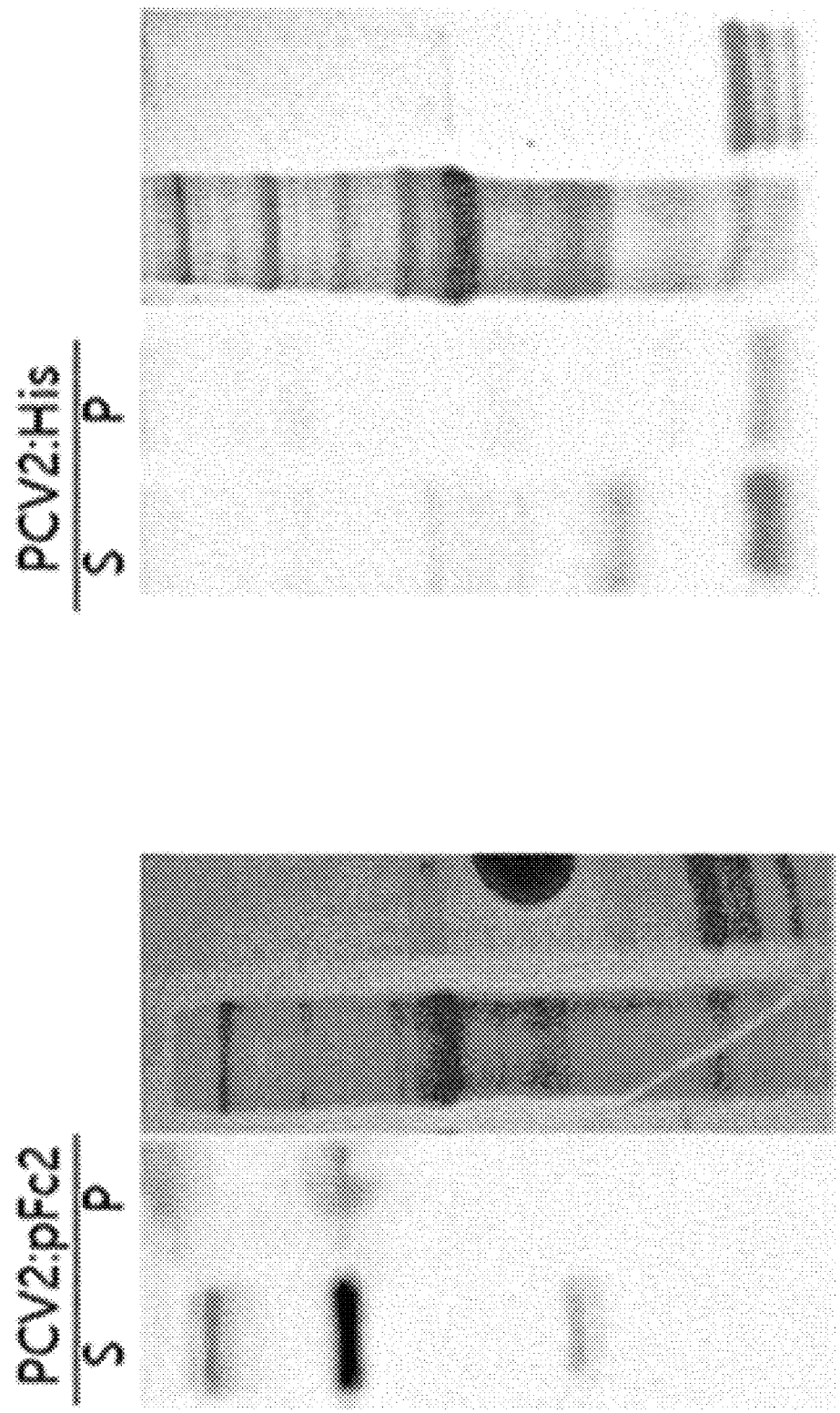
FIG. 7 illustrates western blotting results of confirming the solubility and productivity of a pFc-fused PCV2 recombinant protein according to an embodiment of the present invention.

As illustrated in FIG. 7, it was confirmed that the pFc2-fused PCV2 recombinant protein was mostly included in the solution and exhibited significantly increased productivity as compared to that of the His-tag-fused PCV2 recombinant protein.

Example 5: Experiment for pFc2-Fused E2 Recombinant Protein Expression 5.1. Isolation of pFc2-Fused Antigen Protein To confirm whether the pFc2 fragment is fused to an antigen protein and usable, a polynucleotide (SEQ ID NO: 17) encoding an E2 protein, which is a swine fever antigen, was inserted instead of the VP1 gene of FMDV included in the expression vector of Example 1 to prepare an expression vector expressing a BiP:E2:pFc2 recombinant protein. Then, *Arabidopsis thaliana* was transformed with the prepared expression vector by an *Agrobacterium*-mediated transformation method, *Arabidopsis thaliana* with resistance to kanamycin was selected, and homo-seeds in which the pFc2-fused E2 recombinant protein was stably expressed through generation advancement were finally obtained, thereby completing the preparation of a transformed plant. Then, proteins were isolated from 8 g of the finally obtained transformed plant by using a protein extraction buffer commonly used in protein extraction, and the pFc-fused E2 recombinant protein was isolated using AKTA prime (GE Healthcare) equipped with a Protein A-Sepharose column. Then, as a control, a BiP:E2:CBD recombinant protein produced by fusion of a CBD (SEQ ID NO: 19) instead of the pFc fragment was used. The CBD-fused E2 recombinant protein was isolated from 5 g of the transformed plant using amorphous cellulose (AMC). Thereafter, the isolated recombinant protein was dialyzed with phosphate buffered saline (PBS), and then concentrated using a centrifugal filter tube. To measure the amount of the isolated recombinant protein, the protein was subjected to SDS-PAGE and then Coomassie Blue staining. At this time, the recombinant protein was quantified using a standard curve using bovine serum albumin (BSA). The results thereof are illustrated in FIG. 8.

Figure 8:
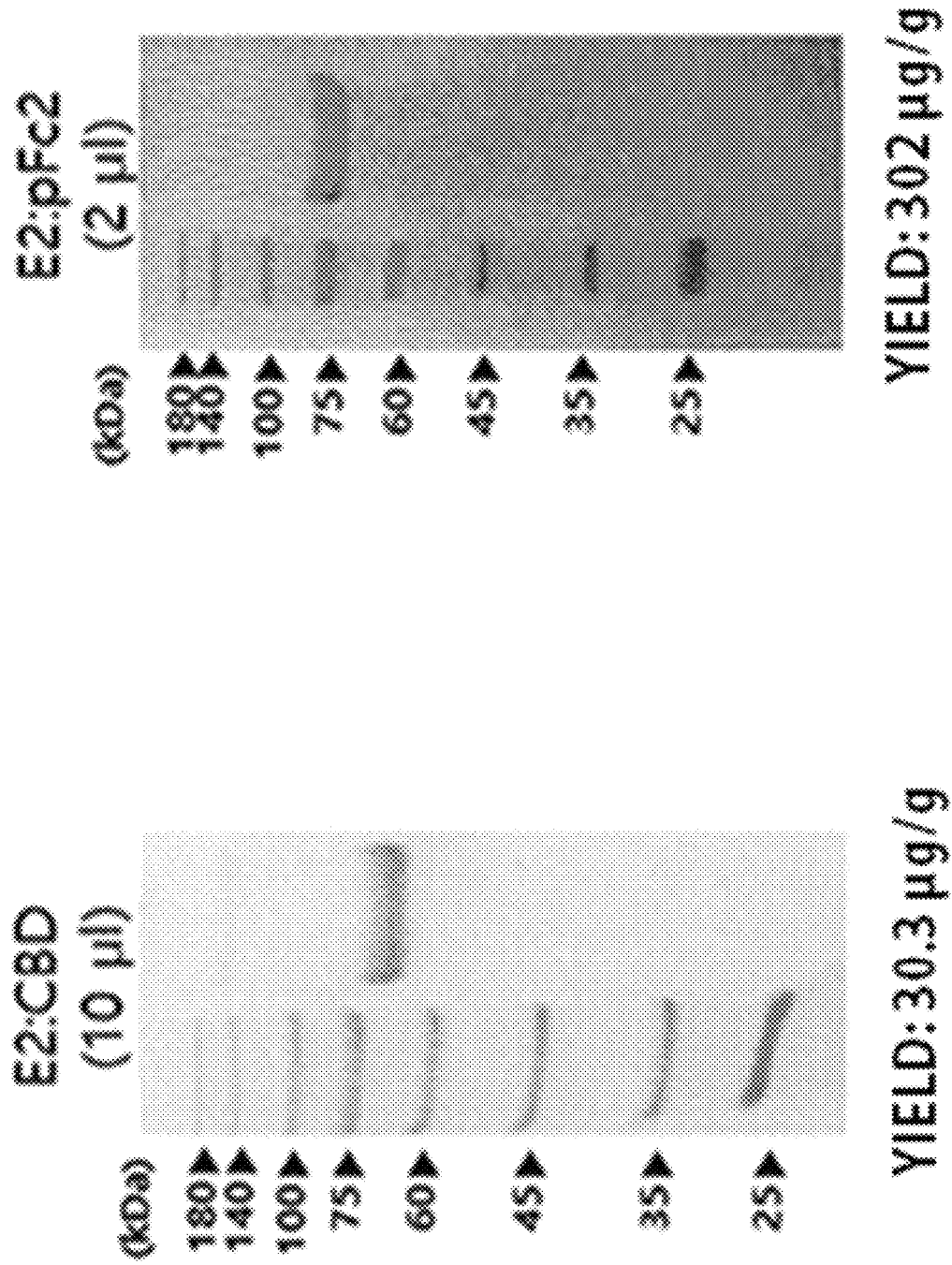
FIG. 8 illustrates results of confirming the productivity of a pFc-fused E2 recombinant antigen according to an embodiment of the present invention.

As illustrated in FIG. 8, it was confirmed that while the CBD-fused E2 recombinant antigen was produced in an amount of about 30 μg per 1 g of the plant, the pFc2-fused E2 recombinant antigen was produced in an amount of 302 μg per 1 g of the plant. From the above results, it was confirmed that an expression amount of a target antigen could be increased 10-fold or more using the pFc2 fragment.

5.2. Immunogenicity and Virus Neutralization Ability Confirmation Experiment for pFc2-Fused E2 Recombinant Antigen To confirm whether the pFc2-fused E2 recombinant antigen has immunogenicity and virus neutralization ability by inducing an antibody in vivo, experiments were carried out using 6-week-old male C57BL/6J mice. More specifically, experimental group mice were administered 1 μg of the pFc2-fused E2 recombinant antigen once (6-week-old) or twice (6-week-old and 8-week-old), and negative control mice were administered phosphate-buffered solution. In addition, as a positive control, mice were administered the CBD-fused E2 recombinant antigen at the same dose and the same time as those used in the experimental group. Upon administration of each antigen, each antigen was mixed with the same amount of Freund's adjuvant and administered, and a complete adjuvant was administered in the once-administered group and, in the twice-administered group, an incomplete adjuvant was administered after administration of a complete adjuvant. Then, blood was collected at the time when the experiment was started and every week from 1 week after administration of each antigen, and it was examined using an antibody kit for clinical diagnosis for swine fever virus (CSFV-ab ELISA kit, MEDIAN DIAGNOSTICS) whether a specific antibody against the administered antigen was generated and maintained. For the twice-administered group, blood collection was started 1 week after the time when the second administration was completed. Experiments were carried out using five mice per group, and the results thereof are illustrated in Table 1 and FIGS. 9 and 10. In Table 1, the S/P value was determined as positive in the case of a value of 0.14 or more and as negative in the case of a value of less than 0.14.

TABLE 1

| Ag | | S/P value | | | | | | | |
|---|---|---|---|---|---|---|---|---|---|
| | | 1 w | 2 w | 3 w | 4 w | 5 w | 6 w | 7 w | Fn. |
| E2:CBD | Mouse 1 | −0.10 | 0.33 | 0.69 | 1.04 | 1.58 | 1.42 | 1.62 | 1.26 |
| | Mouse 2 | −0.01 | 0.32 | 0.82 | 0.87 | 0.84 | 0.89 | 0.63 | 0.72 |
| | Mouse 3 | −0.07 | 0.90 | 0.89 | 0.80 | 0.85 | 1.21 | 1.41 | 1.47 |
| | Mouse 4 | −0.04 | 0.21 | 0.31 | 0.25 | 0.30 | 0.35 | 0.43 | 1.15 |
| | Mouse 5 | −0.07 | 0.14 | 0.31 | 0.46 | 0.74 | 0.96 | 1.08 | 0.96 |
| E2:pFc2 | Mouse 1 | 0.44 | 1.30 | 2.18 | 2.27 | 2.19 | 2.07 | 1.91 | 2.09 |
| | Mouse 2 | 1.15 | 1.75 | 2.65 | 3.14 | 3.23 | 2.82 | 2.87 | 2.80 |
| | Mouse 3 | 0.06 | 0.57 | 1.25 | 1.40 | 1.17 | 1.08 | 1.11 | 1.06 |
| | Mouse 4 | 0.40 | 1.72 | 2.66 | 2.59 | 2.58 | 2.55 | 2.49 | 3.10 |
| | Mouse 5 | 0.44 | 1.54 | 3.00 | 2.55 | 2.66 | 2.71 | 2.43 | 2.95 |

Figure 9:
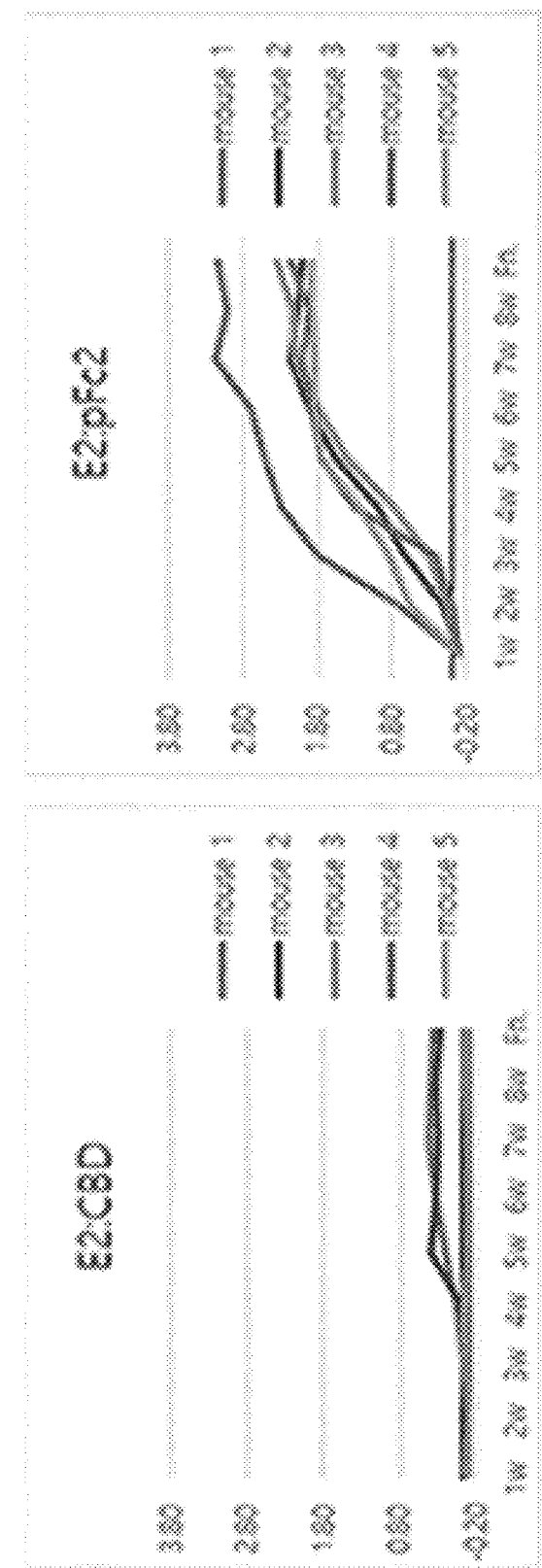
FIG. 9 illustrates results of confirming the immunogenicity of a pFc-fused E2 recombinant antigen according to an embodiment of the present invention, wherein the antigen was administered once.

As illustrated in FIG. 9, it was confirmed that in the case of administering the antigens once, the pFc2-fused E2 recombinant antigen exhibited high reactivity from 1 week after administration and maintained the high activity more than 8 weeks. In contrast, it was confirmed that although the CBD-fused E2 recombinant antigen exhibited positive values, the reactivity thereof was low compared to the pFc2-fused E2 recombinant antigen.

Figure 10:
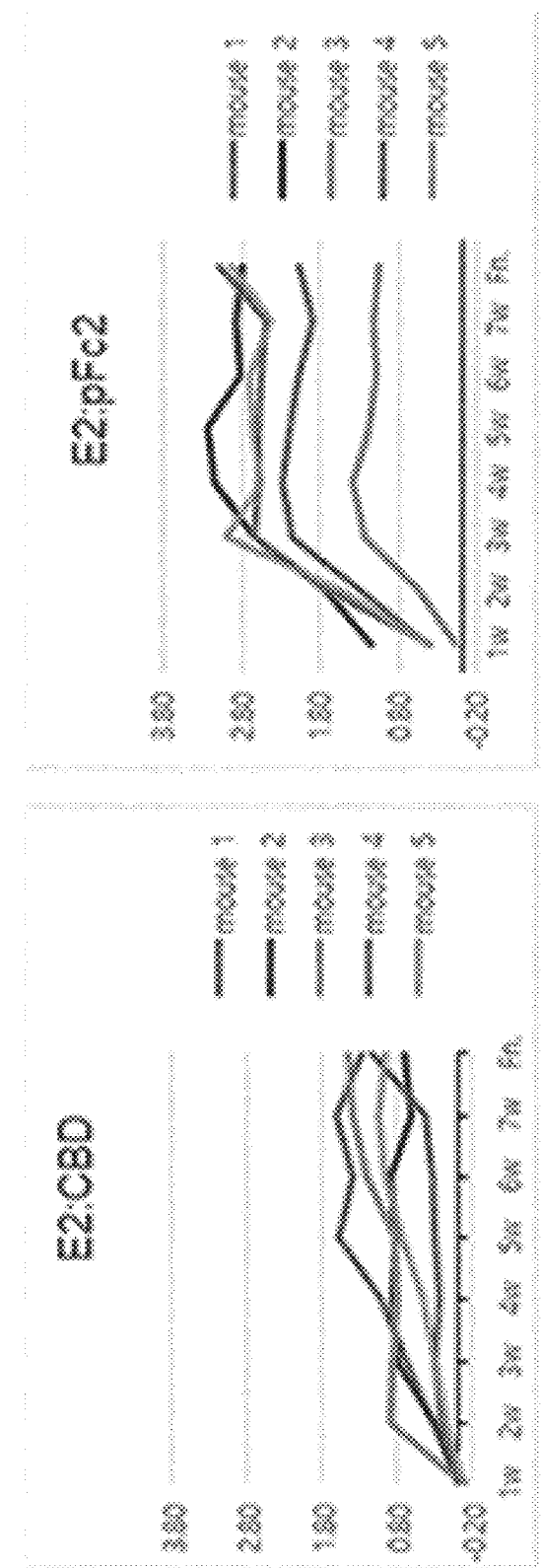
FIG. 10 illustrates results of confirming the immunogenicity of a pFc-fused E2 recombinant antigen according to an embodiment of the present invention, wherein the antigen was administered twice.

As shown in FIG. 10 and Table 1, it was confirmed that, in the case of administering the antigens twice, the CBD-fused E2 recombinant antigen also exhibited increased reactivity as compared to administering once, but still had low reactivity as compared to the pFc2-fused E2 recombinant antigen.

In addition, serum samples of the same mice were sent to the Animal and Plant Quarantine Agency to identify the virus neutralization ability thereof. The results thereof are shown in Table 2 below.

TABLE 2

| Experiment No. | Antigen | Individual No. | Neutralizing antibody value |
|---|---|---|---|
| 2-1st (injected twice) | E2:CBD | 1 | 64 |
|  |  | 2 | 32 |
|  |  | 3 | 32 |
|  |  | 4 | 32 |
|  |  | 5 | 128 |
|  | E2:pFc2 | 1 | 128 |
|  |  | 2 | 256 |
|  |  | 3 | 32 |
|  |  | 4 | 256 |
|  |  | 5 | 512 |
| 2-2nd (injected once) | E2:CBD | 1 | 4 |
|  |  | 2 | 4 |
|  |  | 3 | <4 |
|  |  | 4 | <4 |
|  |  | 5 | <4 |
|  | E2:pFc2 | 1 | 256 |
|  |  | 2 | 256 |
|  |  | 3 | 64 |
|  |  | 4 | 128 |
|  |  | 5 | 64 |
|  | Negative |  | <4 |
|  | Positive |  | 2048 |

As illustrated in Table 2, it was confirmed that while the CBD-fused E2 recombinant antigen exhibited negative values in some mice when the antigen was administered once, the pFc2-fused E2 recombinant antigen exhibited a high potency of virus neutralization ability when administered both once and twice.

5.3. Virus Neutralization Ability Confirmation Experiment for pFc2-Fused E2 Recombinant Antigen To confirm whether the pFc2-fused E2 recombinant antigen also exhibits a high potency of virus neutralization ability in piglets, 4 swine fever antibody-negative piglets were selected and administered the pFc-fused E2 recombinant antigen twice, and serums obtained at intervals of 2 weeks were sent to the Animal and Plant Quarantine Agency to identify virus neutralization ability thereof. The results thereof are shown in Table 3 below.

TABLE 3

| | | Period | | | | | | |
|---|---|---|---|---|---|---|---|---|
| Individual | | 0 week (1st inoculation) Neutralizing antibody | 2 weeks (2nd inoculation) Neutralizing antibody | 4 weeks Neutralizing antibody | 6 weeks Neutralizing antibody | 8 weeks Neutralizing antibody | 10 weeks Neutralizing antibody | 12 weeks Neutralizing antibody |
| E2: pFc2 | #7 | 1 | <1 | 8 | 7 | 7 | 7 | 6 |
|  | #8 | <1 | 1 | 9 | 8 | 7 | 8 | 6 |
|  | #9 | <4 | 4 | 8 | 7 | 6 | 5 | 5 |
|  | #10 | 2 | 4 | 10 | 9 | 7 | 7 | 6 |
|  | Average | 1.5 | 2.25 | 8.75 | 7.75 | 6.75 | 6.75 | 5.75 |

As shown in Table 3, it was confirmed that all piglets exhibited positive values as in the experiments performed using the mice of Example 3.2.

From the above results, it was confirmed that by fusing the pFc2 fragment of the present invention with various peptides or proteins for vaccines, not only the productivity but also solubility and stability of a target antigen were increased, inhibiting the agglomeration of the target antigen, and thus the recombinant antigen is effective in maintaining physiological activity or pharmacological activity thereof. It was also confirmed that by preparing a recombinant antigen by fusing an antigen with a pFc2 fragment, the pFc2 fragment exhibited a self-adjuvanting effect and a self-adjuvant effect, and thus not only the immunogenicity but also productivity and stability of a target antigen could be significantly increased.

The foregoing description of the present invention is provided for illustrative purposes only, and it will be understood by those of ordinary skill in the art to which the present invention pertains that the present invention may be easily modified into other particular forms without changing the technical spirit or essential characteristics of the present invention. Thus, the above-described embodiments should be construed as being provided for illustrative purposes only and not for purposes of limitation.

INDUSTRIAL APPLICABILITY

The present invention relates to an antigen fused with a porcine Fc fragment, and more particularly, to a vaccine composition having a self-adjuvanting effect by binding an Fc fragment to various antigens, and a preparation method thereof. Since the antigens fused with an Fc fragment of the present invention have a self-adjuvanting effect, they can markedly increase the preventive and/or treatment effects of the vaccine composition, so it is expected to be widely usable by applying to various vaccine compositions.

The invention claimed is:

1. A vaccine composition comprising, as an active ingredient, an antigen fused with a porcine Fc fragment consisting of the amino acid sequence of SEQ ID NO: 4.

2. The vaccine composition of claim 1, wherein the antigen has a self-adjuvanting effect and increased solubility through fusion with the Fc fragment.

3. An expression vector of a recombinant antigen having a self-adjuvanting effect, the expression vector comprising a polynucleotide encoding a porcine Fc fragment consisting of the amino acid sequence of SEQ ID NO: 4 and a polynucleotide encoding an antigen.

4. The expression vector of claim 3 further comprising a promotor gene, wherein the promoter gene, the polynucleotide encoding the porcine Fc fragment, and the polynucleotide encoding the antigen are sequentially linked.

5. The expression vector of claim 4, wherein the promoter comprises one or more selected from the group consisting of a 35S promoter derived from cauliflower mosaic virus, a 19S RNA promoter derived from cauliflower mosaic virus, an actin protein promoter of a plant, an ubiquitin protein promoter, a cytomegalovirus (CMV) promoter, a simian virus 40 (SV40) promoter, a respiratory syncytial virus (RSV) promoter, a pEMU promoter, an MAS promoter, a histone promoter, a Clp promoter, and an elongation factor-1 alpha (EF-1α) promoter.

6. The expression vector of claim 3 further comprising comprises a polynucleotide encoding a chaperone binding protein (BiP).

7. The expression vector of claim 3 further comprising comprises a gene encoding a His-Asp-Glu-Leu (HDEL) (SEQ ID NO: 20) peptide.

8. The expression vector of claim 3 further comprising comprises a 5' untranslated region (UTR) site gene of M17.

9. The expression vector of claim 3, wherein the expression vector increases an expression amount and solubility of the Fc fragment-fused antigen.

10. A method of producing a recombinant antigen having a self-adjuvanting effect, the method comprising:

(a) culturing transgenic cells transformed with the expression vector of claim 3; and (b) isolating and purifying a porcine Fc fragment-fused antigen from the transgenic cells or a culture broth thereof.

11. A method of preventing or treating an infectious disease, the method comprising administering, to a subject in need thereof, the composition of claim 1.

* * * * *

SEQUENCE LISTING

<160> NUMBER OF SEQ ID NOS: 20

<210> SEQ ID NO 1
<211> LENGTH: 690
<212> TYPE: DNA
<213> ORGANISM: Artificial Sequence
<220> FEATURE:
<223> OTHER INFORMATION: DNA sequence of pFc1

<400> SEQUENCE: 1

```
ggaactaaga ctaagccacc ttgtcctatt tgtccagggt gcgaggtagc cggtcccagc      60
gtgtttattt ttccaccaaa accaaaggat actttgatga tatctcaaac accggaagtt    120
acttgcgttg tggtcgacgt ttcaaaagag catgccgaag ttcagttctc ttggtatgtg    180
gatggtgtgg aagtgcacac cgctgagaca cgtcctaaag aggaacagtt taactctact    240
tacagagtcg tgtccgtatt gcccattcag catcaagact ggcttaaggg aaaagaattt    300
aaatgtaagg taaataatgt tgatctgcca gcacctataa ctagaaccat ctcgaaagct    360
attggacaat ctagagaacc tcaagtttat acattgcctc ctccagctga ggaactttct    420
agaagtaaag tcactgttac atgcttagtt attggattct atccaccaga tatccatgtt    480
gaatggaaat caaatggtca gcccgaacct gagggcaact acagaacaac accaccacag    540
caagatgtag atggtacttt tttcctctac tcaaaactag ctgttgataa ggctaggtgg    600
gatcatggcg agacatttga gtgtgcagtc atgcacgaag cacttcataa tcactatacc    660
caaaagtcca taagtaagac gcaaggaaag                                     690
```

<210> SEQ ID NO 2
<211> LENGTH: 230
<212> TYPE: PRT
<213> ORGANISM: Artificial Sequence
<220> FEATURE:
<223> OTHER INFORMATION: Amino acid sequence of pFc1

<400> SEQUENCE: 2

```
Gly Thr Lys Thr Lys Pro Pro Cys Pro Ile Cys Pro Gly Cys Glu Val
1               5                   10                  15

Ala Gly Pro Ser Val Phe Ile Phe Pro Pro Lys Pro Lys Asp Thr Leu
            20                  25                  30

Met Ile Ser Gln Thr Pro Glu Val Thr Cys Val Val Asp Val Ser
        35                  40                  45

Lys Glu His Ala Glu Val Gln Phe Ser Trp Tyr Val Asp Gly Val Glu
    50                  55                  60

Val His Thr Ala Glu Thr Arg Pro Lys Glu Glu Gln Phe Asn Ser Thr
65                  70                  75                  80

Tyr Arg Val Val Ser Val Leu Pro Ile Gln His Gln Asp Trp Leu Lys
                85                  90                  95

Gly Lys Glu Phe Lys Cys Lys Val Asn Asn Val Asp Leu Pro Ala Pro
            100                 105                 110

Ile Thr Arg Thr Ile Ser Lys Ala Ile Gly Gln Ser Arg Glu Pro Gln
        115                 120                 125

Val Tyr Thr Leu Pro Pro Pro Ala Glu Glu Leu Ser Arg Ser Lys Val
    130                 135                 140

Thr Val Thr Cys Leu Val Ile Gly Phe Tyr Pro Pro Asp Ile His Val
145                 150                 155                 160

Glu Trp Lys Ser Asn Gly Gln Pro Glu Pro Glu Gly Asn Tyr Arg Thr
                165                 170                 175
```

```
Thr Pro Pro Gln Gln Asp Val Asp Gly Thr Phe Phe Leu Tyr Ser Lys
            180                 185                 190

Leu Ala Val Asp Lys Ala Arg Trp Asp His Gly Glu Thr Phe Glu Cys
        195                 200                 205

Ala Val Met His Glu Ala Leu His Asn His Tyr Thr Gln Lys Ser Ile
    210                 215                 220

Ser Lys Thr Gln Gly Lys
225             230
```

<210> SEQ ID NO 3
<211> LENGTH: 681
<212> TYPE: DNA
<213> ORGANISM: Artificial Sequence
<220> FEATURE:
<223> OTHER INFORMATION: DNA sequence of pFc2

<400> SEQUENCE: 3

```
gttggaagac catgccctat atgtcctgct tgtgaaggtc caggtccctc tgcttttata      60
ttcccaccaa agccgaagga taccttgatg atttcacgta caccacaagt tacttgtgtt    120
gttgtggatg tttcacaaga aaatcctgag gtacaattca gctggtatgt tgatggggta    180
gaagtgcaca ctgcacagac tcgaccaaag gaggcccagt ttaactcgac ttatagagtt    240
gtttctgttc tcccaatcca acacgaagat tggctgaagg caaggaatt tgaatgcaag    300
gttaacaata aagatctacc agcaccaatt accaggatta tttctaaggc aaaaggaccc    360
tccagagagc cccaagttta cacattgtct ccttctgctg aggagcttag tagaagtaaa    420
gtgagcatta cctgcttagt gacgggattc taccctccag acatcgacgt cgaatggaaa    480
tctaatggtc aacctgagcc agaaggtaac tataggacta ctccaccaca acaggacgtc    540
gatggcacat actttcttta ttcaaaactt gctgtcgata aggcaagttg gcaaagagga    600
gatccatttc agtgtgctgt aatgcatgag gctttgcata atcattatac acagaaatca    660
gtttctaaaa cacaagggaa a                                              681
```

<210> SEQ ID NO 4
<211> LENGTH: 227
<212> TYPE: PRT
<213> ORGANISM: Artificial Sequence
<220> FEATURE:
<223> OTHER INFORMATION: Amino acid sequence of pFc2

<400> SEQUENCE: 4

```
Val Gly Arg Pro Cys Pro Ile Cys Pro Ala Cys Glu Gly Pro Gly Pro
1               5                  10                  15

Ser Ala Phe Ile Phe Pro Pro Lys Pro Lys Asp Thr Leu Met Ile Ser
            20                  25                  30

Arg Thr Pro Gln Val Thr Cys Val Val Asp Val Ser Gln Glu Asn
        35                  40                  45

Pro Glu Val Gln Phe Ser Trp Tyr Val Asp Gly Val Glu Val His Thr
    50                  55                  60

Ala Gln Thr Arg Pro Lys Glu Ala Gln Phe Asn Ser Thr Tyr Arg Val
65                  70                  75                  80

Val Ser Val Leu Pro Ile Gln His Glu Asp Trp Leu Lys Gly Lys Glu
                85                  90                  95

Phe Glu Cys Lys Val Asn Asn Lys Asp Leu Pro Ala Pro Ile Thr Arg
            100                 105                 110

Ile Ile Ser Lys Ala Lys Gly Pro Ser Arg Glu Pro Gln Val Tyr Thr
        115                 120                 125
```

Leu Ser Pro Ser Ala Glu Glu Leu Ser Arg Ser Lys Val Ser Ile Thr
    130                 135                 140

Cys Leu Val Thr Gly Phe Tyr Pro Pro Asp Ile Asp Val Glu Trp Lys
145                 150                 155                 160

Ser Asn Gly Gln Pro Glu Pro Glu Gly Asn Tyr Arg Thr Thr Pro Pro
                165                 170                 175

Gln Gln Asp Val Asp Gly Thr Tyr Phe Leu Tyr Ser Lys Leu Ala Val
                180                 185                 190

Asp Lys Ala Ser Trp Gln Arg Gly Asp Pro Phe Gln Cys Ala Val Met
            195                 200                 205

His Glu Ala Leu His Asn His Tyr Thr Gln Lys Ser Val Ser Lys Thr
        210                 215                 220

Gln Gly Lys
225

<210> SEQ ID NO 5
<211> LENGTH: 702
<212> TYPE: DNA
<213> ORGANISM: Artificial Sequence
<220> FEATURE:
<223> OTHER INFORMATION: DNA sequence of pFc3

<400> SEQUENCE: 5
attgagccac cgacacctat ttgtcctgaa atatgctctt gccctgcggc cgaagtttta      60
ggagcaccgt cggtctttct gtttccacct aaacctaagg acattttaat gatctctagg    120
acgcccaagg taacttgtgt tgttgttgat gtttctcaag aagaagctga ggttcaattc    180
tcctggtatg tagacggcgt tcaattgtac accgcacaga ctaggcctat ggaagaacag    240
tttaactcaa catacagagt agtgtccgtg ttgccgatcc aacatcaaga ttggttgaaa    300
ggtaaagagt ttaagtgtaa agtgaacaat aaggatctcc tttctcctat taccagaact    360
ataagtaaag ctaccggacc atctcgggtt ccacaggtct acactcttcc accagcttgg    420
gaggagctta gcaagtcaaa ggtaagcatc acttgtctcg taacgggatt ctatccacca    480
gatattgatg tggaatggca gagtaatggt caacaggaac ccgagggtaa ttaccgaaca    540
actcctcctc agcaggatgt tgacggtact tattttcttt attcaaagct agctgttgat    600
aaagtgagat ggcaacgtgg cgatttgttc cagtgcgcag tcatgcatga ggctcttcat    660
aatcactata cacaaaaatc aatttctaag acacaaggga ag                       702

<210> SEQ ID NO 6
<211> LENGTH: 234
<212> TYPE: PRT
<213> ORGANISM: Artificial Sequence
<220> FEATURE:
<223> OTHER INFORMATION: Amino acid sequence of pFc3

<400> SEQUENCE: 6

Ile Glu Pro Pro Thr Pro Ile Cys Pro Glu Ile Cys Ser Cys Pro Ala
1               5                  10                  15

Ala Glu Val Leu Gly Ala Pro Ser Val Phe Leu Phe Pro Pro Lys Pro
            20                  25                  30

Lys Asp Ile Leu Met Ile Ser Arg Thr Pro Lys Val Thr Cys Val Val
        35                  40                  45

Val Asp Val Ser Gln Glu Glu Ala Glu Val Gln Phe Ser Trp Tyr Val
    50                  55                  60

Asp Gly Val Gln Leu Tyr Thr Ala Gln Thr Arg Pro Met Glu Glu Gln

```
                65                  70                  75                  80
Phe Asn Ser Thr Tyr Arg Val Val Ser Val Leu Pro Ile Gln His Gln
                    85                  90                  95

Asp Trp Leu Lys Gly Lys Glu Phe Lys Cys Lys Val Asn Asn Lys Asp
                100                 105                 110

Leu Leu Ser Pro Ile Thr Arg Thr Ile Ser Lys Ala Thr Gly Pro Ser
                115                 120                 125

Arg Val Pro Gln Val Tyr Thr Leu Pro Pro Ala Trp Glu Glu Leu Ser
        130                 135                 140

Lys Ser Lys Val Ser Ile Thr Cys Leu Val Thr Gly Phe Tyr Pro Pro
145                 150                 155                 160

Asp Ile Asp Val Glu Trp Gln Ser Asn Gly Gln Gln Glu Pro Glu Gly
                165                 170                 175

Asn Tyr Arg Thr Thr Pro Pro Gln Gln Asp Val Asp Gly Thr Tyr Phe
            180                 185                 190

Leu Tyr Ser Lys Leu Ala Val Asp Lys Val Arg Trp Gln Arg Gly Asp
        195                 200                 205

Leu Phe Gln Cys Ala Val Met His Glu Ala Leu His Asn His Tyr Thr
    210                 215                 220

Gln Lys Ser Ile Ser Lys Thr Gln Gly Lys
225                 230

<210> SEQ ID NO 7
<211> LENGTH: 21
<212> TYPE: DNA
<213> ORGANISM: Artificial Sequence
<220> FEATURE:
<223> OTHER INFORMATION: 5'UTR of M17 gene

<400> SEQUENCE: 7
ggcgtgtgtg tgtgttaaag a                                              21

<210> SEQ ID NO 8
<211> LENGTH: 272
<212> TYPE: DNA
<213> ORGANISM: Artificial Sequence
<220> FEATURE:
<223> OTHER INFORMATION: DNA sequence of chapherone binding protein(BiP)

<400> SEQUENCE: 8
atggctcgct cgtttggagc taacagtacc gttgtgttgg cgatcatctt cttcggtgag      60
tgattttccg atcttcttct ccgatttaga tctcctctac attgttgctt aatctcagaa     120
ccttttttcg ttgttcctgg atctgaatgt gtttgtttgc aatttcacga tcttaaaagg     180
ttagatctcg attggtattg acgattggaa tctttacgat ttcaggatgt ttatttgcgt     240
tgtcctctgc aatagaagag gctacgaagt ta                                   272

<210> SEQ ID NO 9
<211> LENGTH: 639
<212> TYPE: DNA
<213> ORGANISM: Artificial Sequence
<220> FEATURE:
<223> OTHER INFORMATION: DNA sequence of FMDV-VP1

<400> SEQUENCE: 9
actacaagta ccggcgaatc tgctgatcca gttactgcta cagttgaaaa ttatggtgga      60
gaaacacaag tgcaaagaag acatcataca gatgtttctt ttatcctaga taggtttgtt    120
aaggtcactc ctaaggattc aattaatgtt ttggacctga tgcagactcc cccacataca    180
```

-continued

```
ttggttggcg ctctacttcg tactgcaact tattatttcg ctgatttaga ggtagccgtt      240
aaacacgaag gtgatttaac atgggttcct aatggagcac ctgaggctgc actcgataat      300
actactaatc caactgctta ccacaaagca ccactcacta gactcgcgct tccttacact      360
gccccgcata gggttcttgc tactgtttat aacgggaact gcaaatacgc aggtggttca      420
ttgcctaatg tacgaggaga tttgcaagta ttggctcaaa aagcagcatg gccattacct      480
acttctttta actatggagc tataaaggct acacgtgtga cggaacttct ttataggatg      540
aagagagctg agacatactg tcctagacca ttactggctg ttcatccatc cgccgcaaga      600
cacaaacaga aaattgtggc tcccgttaag cagagcctt                              639
```

<210> SEQ ID NO 10
<211> LENGTH: 213
<212> TYPE: PRT
<213> ORGANISM: Artificial Sequence
<220> FEATURE:
<223> OTHER INFORMATION: Amino acid sequence of FMDV-VP1

<400> SEQUENCE: 10

```
Thr Thr Ser Thr Gly Glu Ser Ala Asp Pro Val Thr Ala Thr Val Glu
1               5                  10                  15

Asn Tyr Gly Gly Glu Thr Gln Val Gln Arg Arg His His Thr Asp Val
            20                  25                  30

Ser Phe Ile Leu Asp Arg Phe Val Lys Val Thr Pro Lys Asp Ser Ile
        35                  40                  45

Asn Val Leu Asp Leu Met Gln Thr Pro Pro His Thr Leu Val Gly Ala
    50                  55                  60

Leu Leu Arg Thr Ala Thr Tyr Tyr Phe Ala Asp Leu Glu Val Ala Val
65                  70                  75                  80

Lys His Glu Gly Asp Leu Thr Trp Val Pro Asn Gly Ala Pro Glu Ala
                85                  90                  95

Ala Leu Asp Asn Thr Thr Asn Pro Thr Ala Tyr His Lys Ala Pro Leu
            100                 105                 110

Thr Arg Leu Ala Leu Pro Tyr Thr Ala Pro His Arg Val Leu Ala Thr
        115                 120                 125

Val Tyr Asn Gly Asn Cys Lys Tyr Ala Gly Gly Ser Leu Pro Asn Val
    130                 135                 140

Arg Gly Asp Leu Gln Val Leu Ala Gln Lys Ala Ala Trp Pro Leu Pro
145                 150                 155                 160

Thr Ser Phe Asn Tyr Gly Ala Ile Lys Ala Thr Arg Val Thr Glu Leu
                165                 170                 175

Leu Tyr Arg Met Lys Arg Ala Glu Thr Tyr Cys Pro Arg Pro Leu Leu
            180                 185                 190

Ala Val His Pro Ser Ala Ala Arg His Lys Gln Lys Ile Val Ala Pro
        195                 200                 205

Val Lys Gln Ser Leu
    210
```

<210> SEQ ID NO 11
<211> LENGTH: 330
<212> TYPE: DNA
<213> ORGANISM: Artificial Sequence
<220> FEATURE:
<223> OTHER INFORMATION: DNA sequence for GP5

<400> SEQUENCE: 11

```
aacggcaaca gctcgacata ccaatacata taaacttga cggtatgcga gctgaatggg      60
accgcctggt tgtctaccca cttttcttgg gcagtcgaga ccggaggcgg gggtagcaaa     120
aattgtatgg cttgccgcta cgcccgcacc cggttcacca acttcattgt agacgaccgg    180
gggaggattc atcggtggaa gtccccggtg gtggtggaga aatttggcaa agccgaaatt    240
ggcggcggtc ttgtcaccat caaacatgtc gtcctcgaag gggttaaagc tcaaccttg     300 acgaggactt cggctgagca atgggaagcc                                     330
```

```
<210> SEQ ID NO 12
<211> LENGTH: 110
<212> TYPE: PRT
<213> ORGANISM: Artificial Sequence
<220> FEATURE:
<223> OTHER INFORMATION: Amino acid sequence for GP5

<400> SEQUENCE: 12
```

Asn Gly Asn Ser Ser Thr Tyr Gln Tyr Ile Tyr Asn Leu Thr Val Cys
1               5                   10                  15

Glu Leu Asn Gly Thr Ala Trp Leu Ser Thr His Phe Ser Trp Ala Val
            20                  25                  30

Glu Thr Gly Gly Gly Ser Lys Asn Cys Met Ala Cys Arg Tyr Ala
        35                  40                  45

Arg Thr Arg Phe Thr Asn Phe Ile Val Asp Asp Arg Gly Arg Ile His
    50                  55                  60

Arg Trp Lys Ser Pro Val Val Glu Lys Phe Gly Lys Ala Glu Ile
65                  70                  75                  80

Gly Gly Gly Leu Val Thr Ile Lys His Val Val Leu Glu Gly Val Lys
                85                  90                  95

Ala Gln Pro Leu Thr Arg Thr Ser Ala Glu Gln Trp Glu Ala
            100                 105                 110

```
<210> SEQ ID NO 13
<211> LENGTH: 477
<212> TYPE: DNA
<213> ORGANISM: Artificial Sequence
<220> FEATURE:
<223> OTHER INFORMATION: DNA sequence for CBM3

<400> SEQUENCE: 13
```

```
gtatcaggta accttaaggt ggagttttac aactcgaacc cttctgatac aactaactca    60
ataaacccac agttcaaagt tacaaacaca ggcagctctg cgatcgattt gtctaaatta   120
accctcagat actattatac ggttgatgga cagaaggacc agactttctg tgtgatcat    180 gcagctatca ttggttctaa cggtagctac aacggaatta catcaaacgt gaagggcact    240
ttcgttaaga tgtcctctag cactaacaac gcagacacat atttggagat cagttttacg    300 ggggaaccc ttgaaccagg tgctcacgtc cagattcaag aagattcgc taaaaacgac    360 tggtcgaact atacccaaag taatgattac agttttaaat ccgcctcaca atttgttgag    420
tgggatcagg tcactgctta cctgaacggg gttctagtgt ggggaaagga acctggt       477
```

```
<210> SEQ ID NO 14
<211> LENGTH: 159
<212> TYPE: PRT
<213> ORGANISM: Artificial Sequence
<220> FEATURE:
<223> OTHER INFORMATION: Amino acid sequence for CBM3

<400> SEQUENCE: 14
```

Val Ser Gly Asn Leu Lys Val Glu Phe Tyr Asn Ser Asn Pro Ser Asp
1               5                   10                  15

Thr Thr Asn Ser Ile Asn Pro Gln Phe Lys Val Thr Asn Thr Gly Ser
            20                  25                  30

Ser Ala Ile Asp Leu Ser Lys Leu Thr Leu Arg Tyr Tyr Tyr Thr Val
        35                  40                  45

Asp Gly Gln Lys Asp Gln Thr Phe Trp Cys Asp His Ala Ala Ile Ile
    50                  55                  60

Gly Ser Asn Gly Ser Tyr Asn Gly Ile Thr Ser Asn Val Lys Gly Thr
65                  70                  75                  80

Phe Val Lys Met Ser Ser Thr Asn Asn Ala Asp Thr Tyr Leu Glu
                85                  90                  95

Ile Ser Phe Thr Gly Gly Thr Leu Glu Pro Gly Ala His Val Gln Ile
            100                 105                 110

Gln Gly Arg Phe Ala Lys Asn Asp Trp Ser Asn Tyr Thr Gln Ser Asn
        115                 120                 125

Asp Tyr Ser Phe Lys Ser Ala Ser Gln Phe Val Glu Trp Asp Gln Val
    130                 135                 140

Thr Ala Tyr Leu Asn Gly Val Leu Val Trp Gly Lys Glu Pro Gly
145                 150                 155

<210> SEQ ID NO 15
<211> LENGTH: 579
<212> TYPE: DNA
<213> ORGANISM: Artificial Sequence
<220> FEATURE:
<223> OTHER INFORMATION: DNA sequence for PCV2

<400> SEQUENCE: 15
aaaaatggca ttttcaatac acgcctcagt cgaactttg gatatactgt caagcgtact     60
acagtcacca cgccatcttg ggctgtggat atgatgagat ttaagttgga tgactttgtt    120
cctcctggag ggggaaccaa caaaatttct ataccgtttg agtactatag aatcagaaaa    180
gttaaggttg agttctggcc gtgttccccc ataactcagg gtgataggg tgtgggttca     240 actgctgtta ttctagatga taacttcgta cctaaggcca acgcattgac ttatgacccc    300
tatgtaaact actcatctag acatacaatc ccacaacctt tctcctacca ctcgcgttat    360
tttacaccaa agcctgtttt agattctacc attgattatt ccaaccaaa taacaagagg    420 aatcagcttt ggttgagatt acaaacctca cggaacgtgg atcatgtcgg attgggtact    480
gcatttgaaa atagtaagta tgatcaggac tacaatatcc gtgtgacaat gtacgttcaa    540
tttagggaat taatcttaa agacccacca cttaatcca                            579

<210> SEQ ID NO 16
<211> LENGTH: 193
<212> TYPE: PRT
<213> ORGANISM: Artificial Sequence
<220> FEATURE:
<223> OTHER INFORMATION: Amino acid sequence for PCV2

<400> SEQUENCE: 16

Lys Asn Gly Ile Phe Asn Thr Arg Leu Ser Arg Thr Phe Gly Tyr Thr
1               5                   10                  15

Val Lys Arg Thr Thr Val Thr Thr Pro Ser Trp Ala Val Asp Met Met
            20                  25                  30

Arg Phe Lys Leu Asp Asp Phe Val Pro Pro Gly Gly Gly Thr Asn Lys
        35                  40                  45

```
Ile Ser Ile Pro Phe Glu Tyr Tyr Arg Ile Arg Lys Val Lys Val Glu
    50                  55                  60
Phe Trp Pro Cys Ser Pro Ile Thr Gln Gly Asp Arg Gly Val Gly Ser
 65                  70                  75                  80
Thr Ala Val Ile Leu Asp Asp Asn Phe Val Pro Lys Ala Asn Ala Leu
                 85                  90                  95
Thr Tyr Asp Pro Tyr Val Asn Tyr Ser Ser Arg His Thr Ile Pro Gln
            100                 105                 110
Pro Phe Ser Tyr His Ser Arg Tyr Phe Thr Pro Lys Pro Val Leu Asp
        115                 120                 125
Ser Thr Ile Asp Tyr Phe Gln Pro Asn Asn Lys Arg Asn Gln Leu Trp
130                 135                 140
Leu Arg Leu Gln Thr Ser Arg Asn Val Asp His Val Gly Leu Gly Thr
145                 150                 155                 160
Ala Phe Glu Asn Ser Lys Tyr Asp Gln Asp Tyr Asn Ile Arg Val Thr
                165                 170                 175
Met Tyr Val Gln Phe Arg Glu Phe Asn Leu Lys Asp Pro Pro Leu Asn
            180                 185                 190
Pro
```

```
<210> SEQ ID NO 17
<211> LENGTH: 1026
<212> TYPE: DNA
<213> ORGANISM: Artificial Sequence
<220> FEATURE:
<223> OTHER INFORMATION: DNA sequence of E2

<400> SEQUENCE: 17
aacggctagc ctgcaaggaa gattacaggt acgcaatatc atcaaccaat gagatagggc    60
tactcggggc cggaggtctc accaccacct ggaaagaata caaccacgat ttgcaactga   120
atgacgggac cgttaaggcc atttgcgtgg caggttcctt taaagtcaca gcacttaatg   180
tggtcagtag gaggtatttg gcatcattgc ataaggaggc tttacccact tccgtgacat   240
tcgagctcct gttcgacggg accaacccat caactgagga aatgggagat gacttcgggt   300
tcgggctgtg cccgtttgat acgagtcctg ttgtcaaagg aaagtacaat acaaccttgt   360
tgaacggtag tgcttttctat cttgtctgtc aatagggtg acgggtgtt atagagtgca   420
cagcagtgag cccaacaact ctgagaacag aagtggtaaa gaccttcagg agggacaagc   480
cctttccgca cagaatggat tgtgtgacca acagtggaa aaatgaagat ttattctact   540
gtaagttggg gggcaactgg acatgtgtga aggtgaacc agtggtctac acggggggc   600
tagtaaaaca atgcagatgg tgtggctttg acttcaatga gcctgacgga ctcccacact   660
accccatagg taagtgcatt ttggcaaatg agacaggtta cagaatagtg gattcaacag   720
actgtaacag agatggtgtt gtaatcagca cagaggggag tcatgagtgc ttgatcggta   780
acacgactgt caaggtgcat gcatcagatg aaagactggg ccccatgcca tgcagaccta   840
aagagatcgt ctctagtgca ggacctgtaa ggaaaacttc ctgtacattc aactacgcaa   900
aaactttgaa gaacaagtac tatgagccca gggacagcta cttccagcaa tatatgctta   960
agggcgagta tcagtactgg tttgacctgg acgtgactga ccgccactca gattacttcg  1020
cagaag                                                             1026
```

```
<210> SEQ ID NO 18
<211> LENGTH: 341
<212> TYPE: PRT
```

<213> ORGANISM: Artificial Sequence
<220> FEATURE:
<223> OTHER INFORMATION: Amino acid sequence of E2

<400> SEQUENCE: 18

```
Arg Leu Ala Cys Lys Glu Asp Tyr Arg Tyr Ala Ile Ser Ser Thr Asn
1               5                   10                  15

Glu Ile Gly Leu Leu Gly Ala Gly Gly Leu Thr Thr Thr Trp Lys Glu
            20                  25                  30

Tyr Asn His Asp Leu Gln Leu Asn Asp Gly Thr Val Lys Ala Ile Cys
        35                  40                  45

Val Ala Gly Ser Phe Lys Val Thr Ala Leu Asn Val Val Ser Arg Arg
50                  55                  60

Tyr Leu Ala Ser Leu His Lys Glu Ala Leu Pro Thr Ser Val Thr Phe
65                  70                  75                  80

Glu Leu Leu Phe Asp Gly Thr Asn Pro Ser Thr Glu Glu Met Gly Asp
                85                  90                  95

Asp Phe Gly Phe Gly Leu Cys Pro Phe Asp Thr Ser Pro Val Val Lys
            100                 105                 110

Gly Lys Tyr Asn Thr Thr Leu Leu Asn Gly Ser Ala Phe Tyr Leu Val
        115                 120                 125

Cys Pro Ile Gly Trp Thr Gly Val Ile Glu Cys Thr Ala Val Ser Pro
    130                 135                 140

Thr Thr Leu Arg Thr Glu Val Val Lys Thr Phe Arg Arg Asp Lys Pro
145                 150                 155                 160

Phe Pro His Arg Met Asp Cys Val Thr Thr Val Glu Asn Glu Asp
                165                 170                 175

Leu Phe Tyr Cys Lys Leu Gly Gly Asn Trp Thr Cys Val Lys Gly Glu
            180                 185                 190

Pro Val Val Tyr Thr Gly Gly Leu Val Lys Gln Cys Arg Trp Cys Gly
        195                 200                 205

Phe Asp Phe Asn Glu Pro Asp Gly Leu Pro His Tyr Pro Ile Gly Lys
    210                 215                 220

Cys Ile Leu Ala Asn Glu Thr Gly Tyr Arg Ile Val Asp Ser Thr Asp
225                 230                 235                 240

Cys Asn Arg Asp Gly Val Val Ile Ser Thr Glu Gly Ser His Glu Cys
                245                 250                 255

Leu Ile Gly Asn Thr Thr Val Lys Val His Ala Ser Asp Glu Arg Leu
            260                 265                 270

Gly Pro Met Pro Cys Arg Pro Lys Glu Ile Val Ser Ser Ala Gly Pro
        275                 280                 285

Val Arg Lys Thr Ser Cys Thr Phe Asn Tyr Ala Lys Thr Leu Lys Asn
290                 295                 300

Lys Tyr Tyr Glu Pro Arg Asp Ser Tyr Phe Gln Gln Tyr Met Leu Lys
305                 310                 315                 320

Gly Glu Tyr Gln Tyr Trp Phe Asp Leu Asp Val Thr Asp Arg His Ser
                325                 330                 335

Asp Tyr Phe Ala Glu
            340
```

<210> SEQ ID NO 19
<211> LENGTH: 429
<212> TYPE: DNA
<213> ORGANISM: Artificial Sequence
<220> FEATURE:
<223> OTHER INFORMATION: DNA sequence of cellulose binding domain -continued

<400> SEQUENCE: 19

```
tttcgaagtt caccagtgcc tgcacctggt gataacacaa gagacgcata ttctatcatt     60
caggccgagg attatgacag cagttatggt cccaaccttc aaatctttag cttaccaggt    120
ggtggcagcg ccattggcta tattgaaaat ggttattcca ctacctataa aaatattgat    180
tttggtgacg gcgcaacgtc cgtaacagca agagtagcta cccagaatgc tactaccatt    240
caggtaagat tgggaagtcc atcgggtaca ttacttggaa caatttacgt ggggtccaca    300
ggaagctttg atacttatag ggatgtatcc gctaccatta gtaatactgc gggtgtaaaa    360
gatattgttc ttgtattctc aggtcctgtt aatgttgact ggtttgtatt ctcaaaatca    420
ggaacttct                                                            429
```

<210> SEQ ID NO 20
<211> LENGTH: 4
<212> TYPE: PRT
<213> ORGANISM: Artificial Sequence
<220> FEATURE:
<223> OTHER INFORMATION: Amino acid sequence of HDEL peptide

<400> SEQUENCE: 20

His Asp Glu Leu
1